July 2, 1946. F. H. HOWARD Plant Pat. 702
ROSE PLANT
Filed Nov. 7, 1945
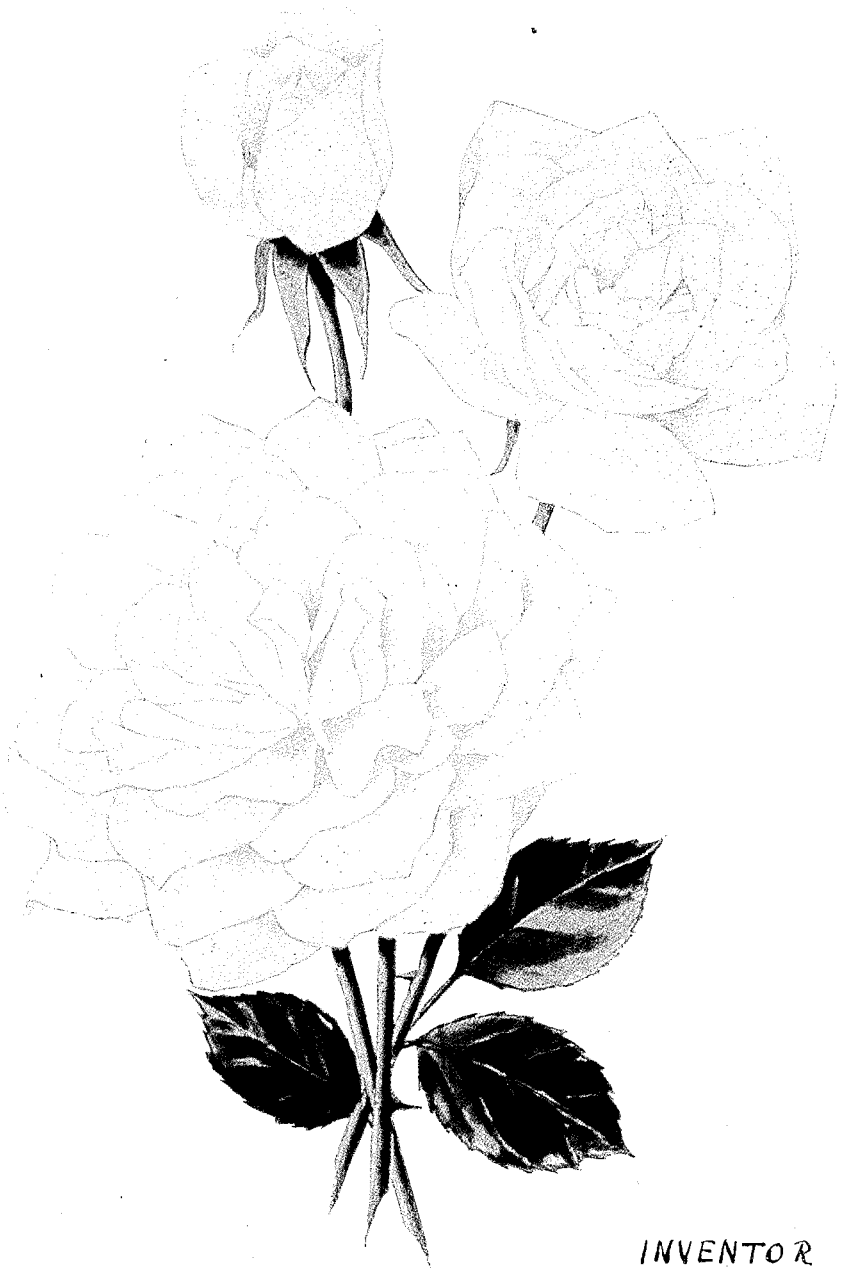
INVENTOR
Frederick Huber Howard
By Orville M. Kile
Plant Pat. Agent Patented July 2, 1946

Plant Pat. 702

UNITED STATES PATENT OFFICE

702

ROSE PLANT

Frederick Huber Howard, Montebello, Calif., assignor to Howard & Smith, Montebello, Calif.

Application November 7, 1945, Serial No. 627,153

1 Claim. (Cl. 47—61)

My present invention relates to a new variety of hybrid tea rose plant, originated as a seedling resulting from a cross of Mrs. J. D. Eisele by Glowing Sunset. Although possessing some of the qualities of each of the parents, my new variety resembles the President Herbert Hoover more than it does either of the parents or any other variety known to me, while at the same time having distinctive features as set forth below.

My new variety has been asexually reproduced for several seasons, and its qualities appear to be permanently fixed.

The accompanying illustration shows three warm-weather specimens of the flower of my new rose plant in various stages of opening and in as nearly the true colors as the artist could show them.

Following is a detailed description of my new variety of rose plant. Color references are to Ridgway's Color Standards and Nomenclature, except where it is obvious that the popular meaning of the term is intended.

*The plant*

Growth:

*Height.*—About 4 feet.

*Form.*—Bush.

*Vigor.*—Very vigorous grower.

Disease resistance: Almost entirely mildew-proof and not subject to black-spot, according to extensive observations made in several different localities throughout the country.

Blooming habit: Continuous and prolific.

Stems:

*Color.*—Light green, with some bronze shading.

*Sturdiness.*—Rigid and upright, holding flowers perfectly erect.

*Thorns.*—Light brown, shading lighter at tips; sharp; outward-pointing.

Foliage:

*Type.*—Five to seven leaflets.

*Size.*—Leaflets are moderate in size, terminal leaflet approximately 2 by 2½ inches. Total length of leaf is about 4 inches.

*Quantity.*—Abundant.

*Color.*—Dark green, with occasional markings of lighter green.

*Shape.*—Oval with acuminate apex; edge sharply serrated.

*Texture.*—Heavy substance.

*Stipules.*—Short and pointed.

*The flower*

Bud:

*Size.*—1½ to 1¾ inches long.

*Shape.*—Conical. Opening bud high centered.

*Color.*—Opening bud approximately Coral Pink (Plate XIII) at tip, with yellow base. Inner surface darker, with some tones as deep as Eugenia Red (Plate XIII).

*Peduncle or neck.*—Rigid; strong. Varying in length but usually short, thus bringing foliage close to flower.

*Sepals.*—Simple; broad. Approximately 1½ inches long.

Bloom:

*Borne.*—Singly.

*Quantity.*—Abundant, averaging 35 to 40 blooms per plant each year.

*Form.*—Pointed in early stages of opening; later camellia-like with inner petals much shorter than outer ones.

*Size.*—Full blown rose approximately 5 inches in diameter in warm weather.

*Petalage.*—45 to 50 petals.

*Longevity.*—Flower keeps perfectly in water for a period of one week. Also lasts well on bush.

*Fragrance.*—Moderate.

Petals:

*Shape.*—Outer petals orbicular, frequently with small point at tip. Edge entire. All petals lie flat rather than undulate.

*Size.*—Outer petals approximately 2 inches in diameter; inner petals smaller and much shorter.

*Texture.*—Very heavy and leathery.

*Color.*—Soft salmon pink overlying a light yellow ground, with suffusion of darker yellow upward from the base. This would fall between Orient Pink (Plate II) and Coral Pink (Plate XIII).

*Arrangement.*—Revolute form in opening bud, expanding to well arranged, evenly disposed petals, building up into a full flower of more or less camellia-like form.

*Behavior.*—Drop cleanly when dead.

Reproductive organs:

*Pistils.*—Numerous. Bunched. Lemon yellow.

*Stamens.*—Numerous, surrounding pistils. *Filaments* about ½ inch in length; lemon yellow. *Anthers* large and dark yellow.

*Comparison*

The known variety most like my new variety is the President Herbert Hoover. The principal features which distinguish my new variety from this and other similar varieties are: The open bud is conical in shape and of medium length rather than long and slender. The bud expands into a large flower with medium sized flat petals in camellia-like form which it holds an unusually long period. The petals are exceedingly thick and of leathery substance in contrast to the light substance of President Herbert Hoover. The flower color is a soft salmon pink, overlying a light yellow ground, with suffusion upward from the yellow base, as distinguished from the multicolored pink and gold shades of the newly opened bud of President Herbert Hoover and the creamy yellow of its open flower. The foliage is much more disease resistant than that of its parents or of President Herbert Hoover.

Having thus disclosed my invention, I claim:

The new and distinct variety of hybrid tea rose plant substantially as herein shown and described, characterized particularly by its prolific blooming habit, its high degree of disease resistance; its conical bud; the heavy substance of its petals and foliage; and the camellia-like form, distinctive salmon pink coloring and long-lasting quality of its flowers.

FREDERICK HUBER HOWARD.